United States Patent
Halpern

(10) Patent No.: US 6,583,310 B1
(45) Date of Patent: Jun. 24, 2003

(54) DIRECT ESTERIFICATION OF AMMONIUM SALTS OF CARBOXYLIC ACIDS

(75) Inventor: Yuval Halpern, Skokie, IL (US)

(73) Assignee: The United States of America as represented by the United States Department of Energy, Washington, DC (US)

( * ) Notice: Subject to any disclaimer, the term of this patent is extended or adjusted under 35 U.S.C. 154(b) by 0 days.

(21) Appl. No.: 10/079,527

(22) Filed: Feb. 22, 2002

(51) Int. Cl.[7] ............................................. C07C 67/03
(52) U.S. Cl. ........................................ 560/60; 560/179
(58) Field of Search .................................. 560/60, 179

(56) References Cited

U.S. PATENT DOCUMENTS 2,565,487 A * 8/1951 Filachione et al. ......... 260/484

FOREIGN PATENT DOCUMENTS

EP 517 571 * 6/1992 ........... C07C/67/08

OTHER PUBLICATIONS

J. Amer. Chem. Soc., 1951, vol. 73 (11), p. 5265–67.*

Ind. Eng. Chem., vol. 44(9), p.2189–91.*

* cited by examiner

*Primary Examiner*—Brian Davis
(74) *Attorney, Agent, or Firm*—Joy Alwan; Thomas G. Anderson; Paul A. Gottlieb

(57) ABSTRACT

A non-catalytic process for producing esters, the process comprising reacting an ammonium salt of a carboxylic acid with an alcohol and removing ammonia from the reaction mixture. Selectivities for the desired ester product can exceed 95 percent.

9 Claims, 1 Drawing Sheet

DIRECT ESTERIFICATION OF AMMONIUM SALTS OF CARBOXYLIC ACIDS

CONTRACTUAL ORIGIN OF INVENTION

The United States Government has rights in this invention pursuant to Contract No. W-31-109-ENG-38 between the U.S. Department of Energy and the University of Chicago, representing Argonne National Laboratory.

BACKGROUND OF THE INVENTION

1. Field of the Invention

This invention relates to an improved process for the esterification of organic acids, and, more specifically, this invention relates to an improved process for the direct esterification of ammonium salts of organic acids.

2. Background of the Invention

Environmental concerns call for the development of relatively non-toxic, biodegradable solvents for paint and grease removal. Ethyl lactate is a non-toxic biodegradable solvent that solubilizes several paint resins.

Esterification of organic acids with alcohol is a reversible process, as depicted in Equation 1, infra.

$$RCOOH + R'OH \rightleftharpoons RCOOR' + H_2O \qquad \text{Eq. 1}$$

where RCOOH is a carboxylic acid and R'OH is an alcohol. Shifting of the equilibrium to the right is achieved by the removal of water produced in the reaction. Simple distillation of the water is effective where none of the other components (starting materials and ester) boils at a temperature below or close to the boiling point of water.

In many cases, carboxylic acid salts and lower boiling reactants must be utilized to produce specific size lactates. The water distillation process described supra does not accommodate some of these lower-boiling reactants. As an alternative, low temperature processes to produce ester compounds such as ethyl lactate exist. However, these low temperature processes tend to give low yields and are expensive. Given this current state of the art, a greater utilization of esters as organic solvents will not occur without a substantial reduction in the cost of production.

One route to the production of ethyl lactate is via the utilization of ammonium lactate as a feedstock. Ammonium lactate is a very desirable and inexpensive reactant because lactic acid and ammonium lactate are produced on a commercial scale by fermentation of carbohydrates during, for example, the production of cheese from milk. The least expensive process for producing ethyl lactate is directly from ammonium or calcium lactate, via the reactions depicted in Equations 2 and 3, respectively:

$$RCOO^-NH_4^+ + R'OH \rightarrow RCOOR' + H_2O + NH_3 \qquad \text{Eq. 2}$$

$$(RCOO^-)_2Ca^{2+} + 2R'OH \rightarrow 2RCOOR' + Ca(OH)_2 \qquad \text{Eq. 3}$$

wherein R is $CH_3(OH)CH$, and R' is $CH_3CH_2$. As can be noted in Table 1, infra, the desired esterification rate is extremely low.

Another drawback to using ammonium lactate as a feedstock is that relatively large amounts of it are converted to the undesired lactamide. Table 1 displays conversion and selectivity results for such a situation. The formation of lactamide from the attempted conversion of ammonium lactate to ethyl lactate lowers the selectivity of the reaction, causes loss of desired product, requires extra separation steps, and forms additional chemical waste which has to be disposed of.

TABLE 1

Conversion[a] and Selectivity[b] for Ethyl Lactate from Ammonium Lactate at Reflux Temperature, as a Function of time (Condenser cooled to −3° C.)

| Time (hrs.) | Conversion (%) | Selectivity (%) |
|---|---|---|
| 0 | 0 | NA |
| 24.2 | 13 | 97 |
| 46.1 | 9 | 75 |
| 53.3 | 11 | 80 |
| 119.6 | 9 | 66 |

[a]Conversion is defined here as the ratio of the moles of ethyl lactate and lactamide produced in the reaction to the initial moles of ammonium lactate expressed in percentage.
[b]Selectivity is defined here as the ratio of moles of ethyl lactate to the sum of the moles of ethyl lactate and lactamide produced in the reaction expressed in percentage.

Filachione, et al. describe a method of preparation of esters from ammonium salts of carboxylic acids; however all the alcohols used had boiling points and overall reaction temperatures well in excess of 100° C. (up to 194° C.) so as to facilitate the removal of ammonia and water. Filachione, E. M.; Costello, E. J.; Fisher, C. H., "Preparation of Esters by Reaction of Ammonium Salts with Alcohols," *J. Amer. Chem. Soc.*, 5265–67 (1951). Filachione, E. M.; Costello, E. J., "Lactic Esters by Reaction of Ammonium Lactate with Alcohols," *Ind. Eng. Chem.*, 2189–91 (1952).

European Patent Appl. EP 517,571 awarded to Alas on Dec. 9, 1992 discloses the synthesis of methyl lactate, butyl lactate, and iso-butyl lactate from optically active ammonium lactate, but does not disclose a synthesis of ethyl lactate.

U.S. Pat. Nos. 5,252,473 and 5,071,754 awarded to Walkup, et al. on Oct. 12, 1993 and on Dec. 10, 1991, respectively, disclose a process for the preparation of ethyl lactate directly from ammonium lactate and ethanol. This method requires the use of $CO_2$ as a catalyst.

U.S. Pat. No. 6,160,173 awarded to Eyal, et al. on Dec. 12, 2000 discloses a process for the recovery of lactic acid esters and amides from aqueous solutions of lactic acids and/or salts.

U.S. Pat. No. 5,723,639 awarded to Datta, et al. on Mar. 3, 1998 discloses a low temperature process for esterifying ammonium and amine-containing salts whereby the salt is reacted with an alcohol in the presence of heat and a catalyst and then subjected to a dehydration and deamination process using pervaporation.

U.S. Pat. No. 5,210,296 awarded to Cockrem, et al. on May 11, 1993 discloses a process for the production of high purity lactate ester or lactic acid from a concentrated fermentation broth by continuous acidification in the presence of alcohol diluent with sequential or simultaneous esterification, distillation off of high purity ester.

U.S. Pat. No. 4,596,889 awarded to Kroener, et al. on Jun. 24, 1986 discloses a process for the preparation of an alkenyl-lactic acid ester by reaction of a cyanohydrin with an alcohol in the presence of hydrogen chloride, followed by hydrolysis.

U.S. Pat. No. 4,314,947 awarded to Hohenschutz, et al. on Feb. 9, 1982 discloses a process for completing the esterification of carboxylic acids with alcohols which employs conventional acid catalysts and water-entraining agents.

None of the aforementioned patents discloses a non-catalytic esterification process.

A need exists in the art for a simple esterification process which does not employ large quantities of solvents, which eliminates competing products, and which is non-catalytic and inexpensive.

SUMMARY OF THE INVENTION

It is an object of the present invention to provide a process for the esterification of a carboxylic acid with an alcohol that overcomes many of the disadvantages of the prior art.

Another object of the present invention is to provide a non-catalytic process for producing lactates. A feature of the invention is its operation at or below 100° C., often at condenser temperatures of −3° C. to 15° C. An advantage of this invention is that low boiling alcohols ($C_1$–$C_4$) can be utilized under reflux conditions to produce similar carbon length esterified moieties.

Still another object of the present invention is to provide a facile, non-catalytic method for producing relatively pure lactic acid esters from a mixture of carboxylic acid ammonium salts and alcohol. A feature of the invention is the rapid removal of ammonia. An advantage of this method is the facile, non-catalytic synthesis of relatively pure lactic acid esters in high yield.

Yet another object of the present invention is the preparation of carboxylic esters from carboxylic acid ammonium salts and alcohol with high selectivity approaching 100%. A feature of this invention is the elimination of competing species through their rapid removal by the utilization of a chemically inert carrier fluid during refluxing and the use of a drying agent to remove water. An advantage of this process is that it obviates the need for resource intensive removal of such byproducts as amides.

Another object of the present invention is to provide a low-cost process for the preparation of lactates. A feature of this invention is the absence of a catalyst and low operating temperatures. An advantage of this process is that it is simple and inexpensive.

Briefly, the invention provides a non-catalytic process for producing esters, the process comprising reacting an ammonium salt of an acid with an alcohol; removing ammonia from the reaction mixture during refluxing conditions; and removing water from the reaction mixture during refluxing conditions.

The invention also provides a device for esterifying carboxylic acids, the device comprising a condenser; a reaction vessel in fluid communication with said condenser; a soxhlet extractor positioned intermediate said condenser and said reaction vessel, said soxhlet extractor containing a drying agent; a means for injecting inert fluid into the device; and a means for evacuating inert fluid from the device.

DESCRIPTION OF THE DRAWING

The present invention together with the above and other objects and advantages may best be understood from the following detailed description of the embodiment of the invention illustrated in the drawings, wherein.

DETAILED DESCRIPTION OF THE INVENTION

Figure 1:
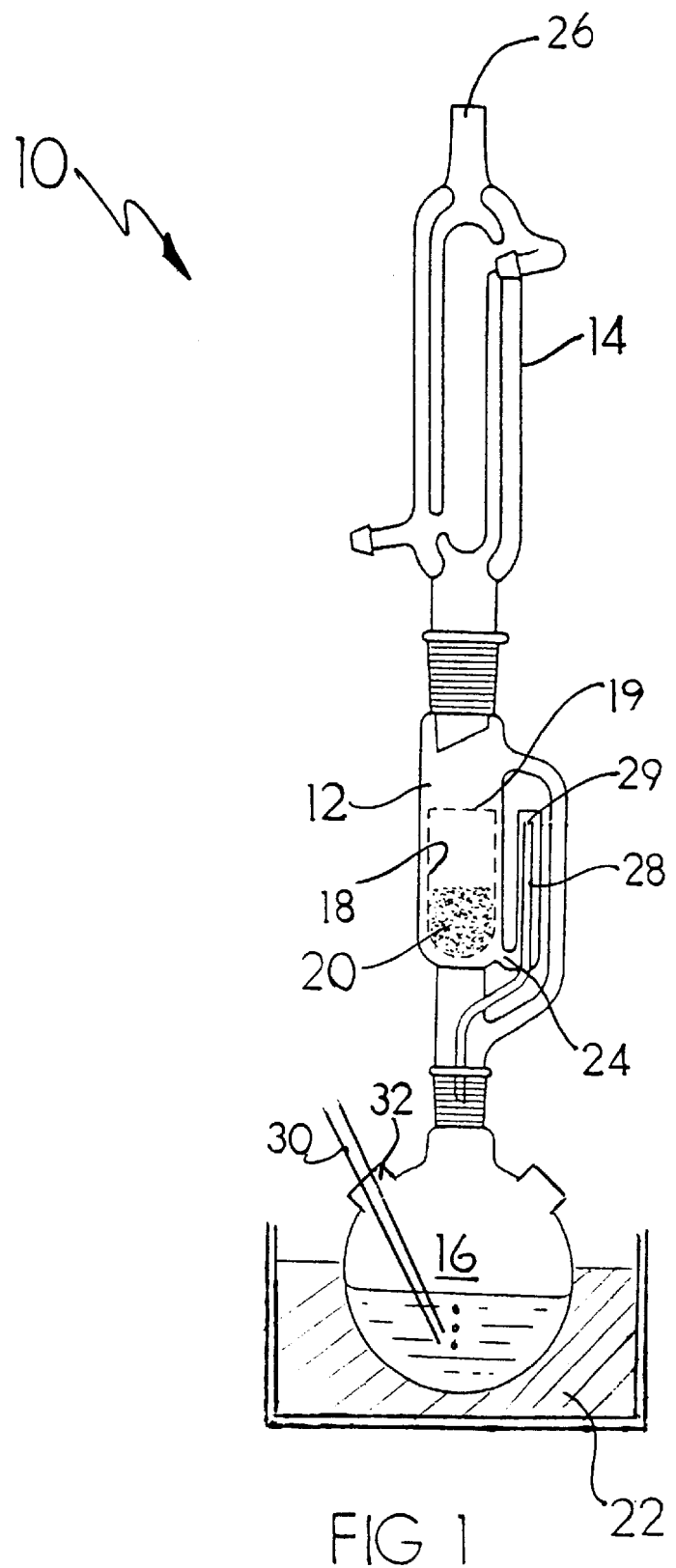
FIG. 1 is a diagram of a soxhlet extraction apparatus, in accordance with features of the present invented method.

The invention provides a non-catalytic process for the direct esterification of fermentation-derived organic acids. Specifically, the invented method provides a process for producing ethyl lactate directly from various lactates, such as ammonium, methylammonium, dimethylammonium, trimethylammonium, and ethylammonium lactates. The invented process has resulted in a conversion rate approaching 50 percent and a selectivity exceeding 95 percent. Conversion is defined herein as the ratio (presented in percent) of the sum of the moles of ethyl lactate and lactamide produced in the reaction to the initial moles of the lactate salt (i.e., ammonium lactate). Selectivity is defined herein as the ratio (presented as percent) of moles of desired product (i.e. ethyl lactate) to the sum of the moles of all conceivable desired and undesired product (i.e. ethyl lactate and lactamide, respectively).

The process involves the reaction of the ammonium salt of a carboxylic acid with an alcohol while a means is employed to remove the alkaline moiety of the salt from the reaction mixture as soon as it is formed.

Reaction Liquor Detail

In the reaction mixture, the molar ratio of alcohol to carboxylic acid is between 1:1 to 10:1, respectively. Suitable carboxylic acids include, but are not limited to, aliphatic acids such as formic acid, acetic acid, propanoic acid, butanoic acid, lactic acid, pentanoic acid, and hexanoic acid; and aromatic acids such as benzoic acid, naphthoic acid, toluic acid, and phthalic acid. Suitable alcohols for use with the invented process include those having from 1 to 4 carbons. Such suitable alcohols include, but are not limited to, aliphatic alcohols such as methanol, ethanol, n-propanol, isopropanol, n-butanol, isobutanol, and t-butanol.

The inert fluid is bubbled through the mixture at a flow rate of approximately 1 milliliters (mL) per minute (min) to 500 mL/min. The role of the inert fluid is to drive off ammonia and thus eliminate amides as competing products. Inert fluids include, but are not limited to gases, such as nitrogen, helium, argon, dry air, or a combination thereof.

The process is novel in that amides are all but eliminated as by-products, thus making product selectivity greater than 95%.

The inventor found that product conversion can be further improved by removing water during recycling of the distillate formed during refluxing. An exemplary means for removing water is a drying agent which extracts water from the distillate during its recycling. The drying agent functions by the adsorption and absorption of water into the drying agent. The water-attractive qualities of the agent depends upon the size of the molecules present with the water in the distillate, the ability of the agent to form hydrogen bonding with the water molecules, and the pore size of the drying agent. Alcohols are not absorbed into the drying agent.

A suitable drying agent is an inert porous substance. Exemplary substances include, but are not limited to diatomaceous earth, molecular sieve, and zeolites. Any inert, porous substance compatible with the environs of the inside of a soxhlet extractor at the temperature ranges discussed herein is appropriate. Commercially available substances having a surface area of between approximately 12 $cm^2$/gram to 20 $cm^2$/gram are also appropriate.

FIG. 1 shows a soxhlet extractor configuration, designated as numeral 10, that is utilized to facilitate the high conversion rates of the invented method. Salient features of the device include a soxhlet apparatus 12 situated intermediate to a condenser 14 and a reaction vessel 16. Prior to initiation of the process, a drying agent 20 is placed in a porous thimble 18 (depicted as an upwardly facing cup) in the soxhlet apparatus. The thimble 18 sits on the bottom of the inner tube of the apparatus 12.

Passage of liquid from the thimble back to the reaction vessel 16 is facilitated via a conduit 24 situated inferior to a depending exterior surface of the porous container 18. In fluid communication with the conduit is an upwardly extending tube 28 terminating at one end 29 in a first opening. A second opening 31 of the tube depends downwardly and into the reaction chamber 16. As such the tube 28 provides fluid communication between the thimble region and the reaction vessel 16. The first opening 29 is slightly below the height of the lip 19 of the thimble 18 so as to facilitate thimble drainage through the porous structure of the thimble instead of over the top of the thimble.

Ingress of the inert fluid is via a conduit 30 permeating a stopper, septum or other means positioned in an access port of the reaction chamber 32.

During the reaction process, the water-containing alcohol condenses and drips onto the drying agent within the porous thimble. Water is absorbed and the anhydrous alcohol slowly fills the body of the apparatus 12. When the alcohol permeates through the sides and bottom of the thimble, the alcohol exits the thimble area via the conduit 24 and finally reaches the top of the tube 28. At that point, the alcohol siphons over into the reaction vessel 16.

The invented method can be conducted at temperatures ranging from 50° C. to 200° C. with the higher temperatures utilized to accommodate higher boiling alcohols. Preferably, the invented process is conducted at temperatures ranging from 60° C. to 110° C. Generally, laboratory scaled experiments were carried out with the reaction vessel at least partially immersed in an oil bath 22.

The esterification of carboxylic acid with alcohol is carried out under reflux conditions (approximately 50° C. to 200° C., again depending on the alcohol) for up to 150 hours. The inventor has found that a molar ratio of 5:1 of alcohol to ammonium salt gives both high yields and high selectivities. Reaction times are determined empirically, but generally can vary from 1 hour to 150 hours. The condenser fluid should be at a temperature suitable to confine the alcohol reactant to the reaction zone (the liquid in the reaction vessel 16) as long as possible. Generally, condenser fluid temperatures of approximately 20° C. to −10° C. are suitable.

The inventor found that subjecting the refluxing reaction mixture to an inert fluid (such as nitrogen gas) accelerates the formation of the desired lactate, and practically prevents the formation of the undesired lactamide. The inert fluid serves as a means for removing the ammonia from the reaction liquor and enters via an injection point 30. Generally, the ammonia is removed via a means of egress 26 from a region of the condenser 14. FIG. 1 depicts the means of egress 26 as situated superior to the rest of the device. As such, the ammonia, first formed by the dissociation of the ammonium salt, is no longer available to react.

EXAMPLE

A 250 mL, three neck round-bottom flask equipped with a soxhlet extraction apparatus through the center neck and a condenser on top of the soxhlet apparatus was placed above an oil bath. A 150 gram (g) solution of ammonium lactate in ethanol was introduced into the round-bottom flask. The masses of reactants gave a molar ratio of 5:1 of alcohol to salt. The reaction mixture was stirred via the magnetic stirrer and a magnetic stir-bar. Experiments were started by immersing ⅔ of the reaction flask in the preheated (110° C.) and stirring oil-bath. Condenser fluid temperatures were either 150° C. or −3° C. The number of moles of each product was determined via liquid chromatography.

Table 1 supra displays results obtained when an inert fluid is not used. In addition, a soxhlet extractor was not used for the trial of Table 1. For all tables, the molar ratio of ethanol to ammonium lactate is 5:1. Tables 2–5 infra examine conversion and selectivity as a function of time for the aforementioned example's conditions, and display the results obtainable from the instant invention when an inert fluid such as nitrogen is continuously bubbled through the mixture.

As can be seen in Tables 2–5 infra, bubbling an inert fluid (e.g., nitrogen) through the reaction mixture during refluxing, accelerates the formation of the desired ethyl lactate, and practically prevents the formation of the undesired lactamide.

TABLE 2

Conversion and Selectivity as a Function of time[a]
(Condenser cooled to −3° C.)

| Time (hrs) | Conversion (%) | Selectivity (%) |
|---|---|---|
| 0 | 0 | NA |
| 6.1 | 1.1 | 66.1 |
| 24.0 | 10.6 | 92.3 |
| 30.1 | 14.3 | 93.2 |
| 48.0 | 21.3 | 94.4 |
| 54.4 | 25.5 | 94.3 |
| 72.0 | 31.4 | 95.1 |
| 78.2 | 34.6 | 94.8 |
| 96.0 | 38.5 | 95.2 |

[a]Nitrogen flow-rate = 200 mL/min

TABLE 3

Conversion and Selectivity as a Function of time[a]
(Condenser cooled to −3° C.)

| Time (hrs.) | Conversion (%) | Selectivity (%) |
|---|---|---|
| 0 | 0 | NA |
| 19.0 | 7.1 | 93.5 |
| 26.1 | 12.0 | 93.2 |
| 43.1 | 24.2 | 91.0 |
| 50.7 | 27.1 | 93.7 |
| 67.1 | 35.8 | 93.5 |
| 74.3 | 40.8 | 93.6 |
| 92.0 | 45.8 | 93.8 |
| 96.0 | 45.3 | 93.6 |

[a]Nitrogen flow-rate = 150 mL/min

TABLE 4

Conversion and Selectivity as a Function of time[a]
(Condenser cooled to −3° C.)

| Time (hrs) | Conversion (%) | Selectivity (%) |
|---|---|---|
| 0 | 0 | NA |
| 6.0 | 1.8 | 89.6 |
| 24.0 | 13.3 | 91.6 |
| 30.0 | 17.8 | 90.5 |
| 48.0 | 28.1 | 91.4 |
| 54.0 | 31.5 | 91.3 |
| 72.0 | 38.5 | 91.9 |
| 78.0 | 40.8 | 91.7 |
| 96.0 | 45.3 | 92.2 |

[a]Nitrogen flow-rate = 50 mL/min

TABLE 5

Conversion and Selectivity as a Function of time[a]
(Condenser cooled to −3° C.)

| Time (hrs.) | Conversion (%) | Selectivity (%) |
|---|---|---|
| 0 | 0 | NA |
| 6.1 | 1.2 | 19.2 |
| 24.0 | 6.4 | 81.3 |
| 30.0 | 8.8 | 80.9 |
| 48.1 | 10.8 | 79.8 |
| 54.1 | 11.7 | 80.4 |
| 72.0 | 13.0 | 77.7 |
| 78.1 | 13.6 | 77.5 |
| 96.0 | 15.9 | 76.0 |

[a]Nitrogen flow-rate = 0 mL/min

As demonstrated in Tables 2–5, high conversion and selectivity were obtained with a continuous flow of nitrogen gas through the reaction mixtures. A condenser fluid temperature of −3° C. (Tables 2–5) seemed to give good results. Higher condenser temperatures work equally well.

While the invention has been described with reference to details of the illustrated embodiment, these details are not intended to limit the scope of the invention as defined in the appended claims.

What is claimed is:

1. A non-catalytic process for producing ethyl lactate comprising:
   a) reacting an ammonium salt of lactic acid with ethanol in refluxing conditions to create a distillate;
   b) bubbling an inert gas selected from the group consisting of nitrogen, helium, argon, dry air or combinations thereof through the distillate to remove the ammonia, thereby reducing amide production;
   c) condensing the distillate on a temperature exchange surface maintained at a temperature of between approximately −100° C. and 200° C.;
   d) removing water during refluxing of the distillate by contacting the distillate with a drying agent; and
   collecting the ethyl lactate.

2. The process as recited in claim 1 wherein the alcohol is present with the ammonium salt of lactic acid in a molar ratio of between 1:1 and 10:1.

3. The process as recited in claim 1 wherein the reaction time is between approximately 1 to 150 hours.

4. The process as recited in claim 1 wherein the refluxing conditions comprises maintaining the temperature of the process between approximately 50° C. and 200° C.

5. The process as recited in claim 1 wherein the salt and alcohol is present in a mixture and inert fluid is dispersed through the mixture at a flow rate of approximately 1 mL/min to 500 mL/min.

6. The process as recited in claim 1 wherein a drying agent removes the water.

7. The process as recited in claim 6 wherein the drying agent is an inert substance selected from the group consisting of diatomaceous earth, molecular sieve, and zeolites.

8. The process as recited in claim 6 wherein the drying agent is used in conjunction with a soxhlet extractor.

9. The process as recited in claim 8 wherein the drying agent is confined to an alcohol permeable container within the soxhlet extractor.

* * * * *